United States Patent [19]

Hattori et al.

[11] 4,415,952
[45] Nov. 15, 1983

[54] LIGHT SOURCE UNIT FOR AN OPTICAL APPARATUS

[75] Inventors: Shinichiro Hattori, Tokyo; Yasuo Inoue, Hachioji, both of Japan

[73] Assignee: Olympus Optical Co., Ltd., Tokyo, Japan

[21] Appl. No.: 275,519

[22] Filed: Jun. 19, 1981

[30] Foreign Application Priority Data

Jun. 30, 1980 [JP] Japan .................. 55-88635

[51] Int. Cl.³ .............................................. F21V 7/04
[52] U.S. Cl. ...................... 362/32; 362/276;
362/321; 362/802; 362/804
[58] Field of Search ................ 362/32, 276, 321, 802, 362/804

[56] References Cited

U.S. PATENT DOCUMENTS 3,594,061 7/1971 Selvage .
3,760,798 9/1973 Edinger .
3,863,243 1/1975 Skolnick et al. .
4,053,756 10/1977 Takahashi .......................... 362/32
4,209,225 6/1980 Kumiomi et al. .
4,356,534 10/1982 Hattori .............................. 362/32

FOREIGN PATENT DOCUMENTS 18125 10/1980 European Pat. Off. .
27608 4/1981 European Pat. Off. .
2828405 1/1979 Fed. Rep. of Germany .
2927959 1/1980 Fed. Rep. of Germany .

Primary Examiner—Stephen J. Lechert, Jr.
Attorney, Agent, or Firm—Frishauf, Holtz, Goodman & Woodward

[57] ABSTRACT

A light source unit for an endoscope is provided with a light-emitting element and a light receiving element which are provided in an eyepiece section of an endoscope. The light-emitting element is supplied with current modified by a specific frequency from an oscillating circuit and produces a light-intensity modulated light. An output signal from the light receiving element is supplied to a filter circuit and a signal of the specific frequency component is taken out from the filter circuit to be compared with a reference voltage in a Schmidt circuit. When an operator approaches to the light receiving element and enters a range within a predetermined distance from the light receiving element, a light intensity of the light which is emitted from the light emitting element toward the operator, reflected from the operator, and is incident on the light receiving element, becomes large. As a result, a signal level supplied to the Schmidt circuit exceeds a predetermined value. At this time, a signal for turning on a light source is produced from the Schmidt circuit to energize a relay and to close a contact of the relay. Then, electric power is supplied from a power source to the light source to turn on the light source. As a result, an illuminating light is supplied from the light source to a light guide of the endoscope, whereby an area of an objective portion can be observed through an image guide of the endoscope.

14 Claims, 7 Drawing Figures

F I G. 2
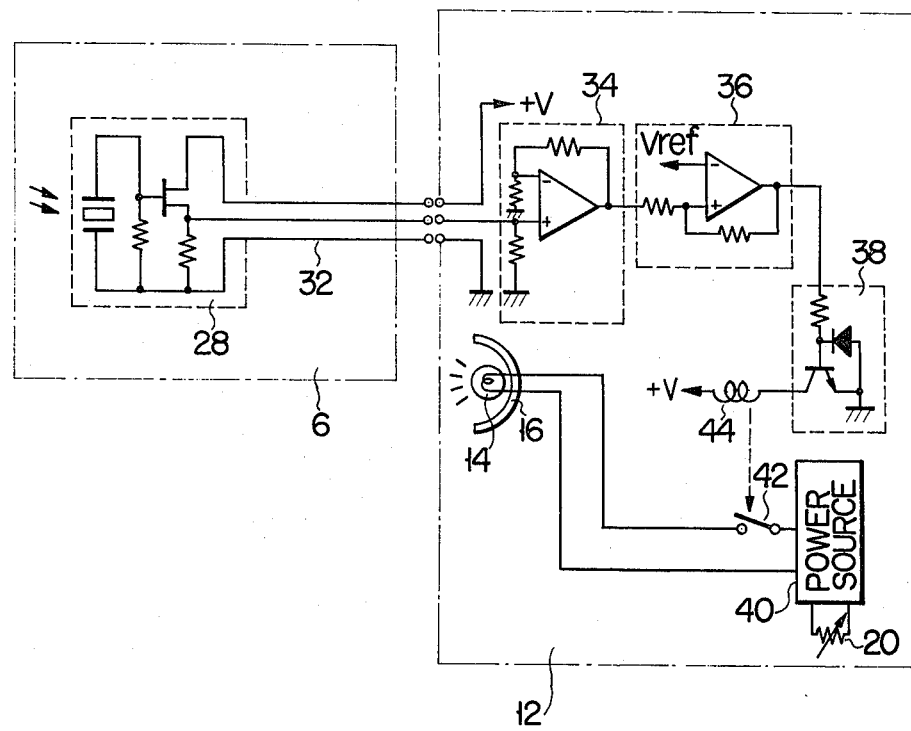
F I G. 3
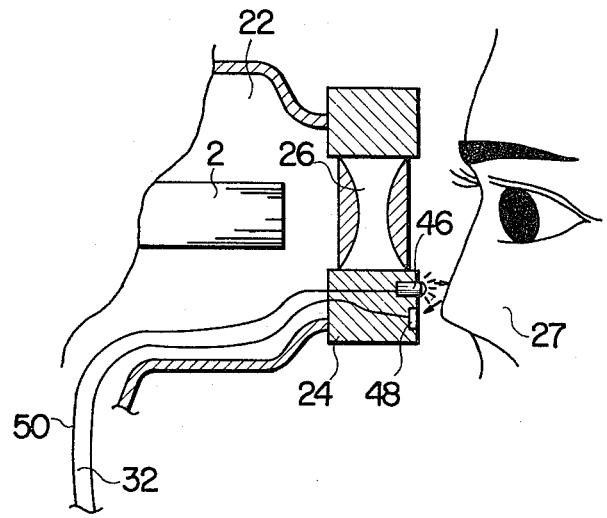

LIGHT SOURCE UNIT FOR AN OPTICAL APPARATUS

BACKGROUND OF THE INVENTION

The present invention relates to a light source unit for an optical apparatus.

Some conventional light source units for endoscopes are provided with a light controller for controlling a brightness of a light source. Therefore, it is possible to control the light source so as to provide a desired brightness when an objective portion is observed. In the light source unit of this type, after a power switch for the light source is turned on and the light source is set to provide a proper light intensity, the light beam is ceaselessly projected in a condensed manner from the light source into a light guide of an endoscope both in an observing mode and a non-observing mode. Because of this continuous condensation, the temperature of the light incident face of the light guide rises. In an extreme case, the light incident face is burned and damaged. Such an accident is more likely to occur as a luminance brightness of the light source is larger and a closed time of the light source switch is longer.

Also in a light source unit for an optical microscope, when a sample is continuously illuminated for a long time, the sample is changed in nature. Further, while texture emitting fluorescent rays are observed, the fluorescence tends to fade. A measure which has been taken to solve the problem, is to turn on the light source switch only at the time of the sample observation or to manually release a shutter provided in an optical path of the light source. The switch or the shutter operation, however, is troublesome for an operator and frequently disturbs him in the observation.

Accordingly, an object of the present invention is to provide a light source unit for an optical apparatus in which a light source unit illuminates a specific area only when the area is observed by the apparatus.

Another object of the present invention is to provide a light source unit for an optical apparatus which is easily operable.

SUMMARY OF THE INVENTION

According to the present invention, there is provided a light source unit for an optical apparatus having an eyepiece section comprising: a light source for illuminating an area to be observed; a power source for supplying electric power to the light source; a sensing means for sensing the approach of an operator to an eyepiece section of an optical apparatus for observing the area; a judging circuit which judges it on an output signal from a sensing means that the operator departs from the eyepiece section by a given distance or more and produces a signal for limiting the illuminating light; and a means for limiting the illuminating light transmitted from the light source to the area by the illuminating light limiting signal.

Other objects and features of the present invention will be apparent from the following description taken in connection with the accompanying drawings.

BRIEF DESCRIPTION OF THE DRAWINGS

FIG. 2 is a circuit diagram of the light source controlling circuit shown in FIG. 1;

FIG. 3 is a schematic diagram of a part of the endoscope system with a light source unit which is another embodiment of the present invention;

DETAILED DESCRIPTION

Figure 1:
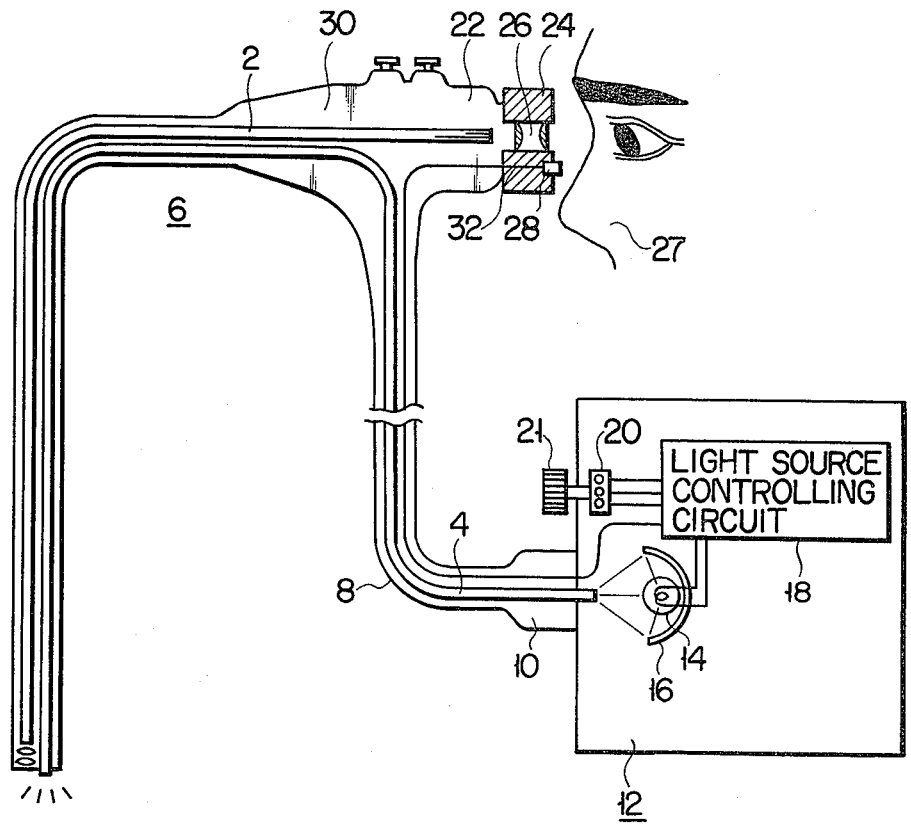
FIG. 1 shows a schematic diagram of an endoscope system with a light source unit which is an embodiment according to the present invention.

FIG. 1 shows a schematic diagram of an endoscope system provided with an embodiment of a light source unit according to the present invention. As well known, a universal cord for an endoscope 6 having an image guide 2 and a light guide 4 is connected to the light source unit 12, through a connector 10. The light guide 4 extending through the universal cord 8 is positioned at the end face within the light source unit 12. Provided within the light source unit 12 are a light source or a lamp 14, and a mirror 16 for condensing light rays emitted from the light source 14 toward the end face of the light guide 4. The light source 14 is connected to a light source control circuit 18 which is connected to a variable resistor 20 for adjusting an intensity of light from the light source 14. A knob 21 provided on a case of the light source unit 12 is attached to the sliding terminal of the resistor 20.

An infrared sensor 28 for sensing infrared rays emitted from an operator, for example, a piezoelectric type sensor, is fixed to an eyepiece frame 24 of an eyepiece section 22 having an eyepiece lens 26 for magnifying an image transmitted, one end face of the image guide 2 being faced to the eyepiece lens 26. The infrared detector 28 is connected to the light source control circuit 18, through signal lines 32 extending in the eyepiece section 22 of the endoscope 6, an operating section 30 and the universal cord 32.

The light source controlling circuit 18 is shown in FIG. 2, for example. The infrared detector 28, comprised of an infrared sensing element, a FET and resistors, is connected to a reference voltage source +V and through signal lines 32 to an input of an amplifier 34 in the light source control circuit 18 made up of an operational amplifier and resistors. The output of the amplifier 34 is connected to one of the input terminals of a Schmidt trigger circuit 36 which is comprised of an operational amplifier and resistors and receives at the other input terminal a reference voltage Vref. The output of the Schmidt trigger circuit 36 is connected to a relay drive circuit 38 comprised of a transistor, a diode and a resistor. Inserted between the circuit 38 and the reference voltage source +V is a relay 44 with a relay contact 42 inserted between the light source lamp 14 and an electric power source 40 for the light source. Connected to the power source 40 is the variable resistor 20 for regulating an electric power supplied, as previously stated.

The light source unit for the endoscope as mentioned above operates as follows. Upon turning on a power switch (not shown) for the light source unit, the light source unit is operated, but the relay 44 is not yet energized with the contact 42 being open. Therefore, the light source lamp 14 is still in a turned-off state. When the operator 27 approaches the eyepiece frame 24 of the endoscope 6 for observing an objective portion in a body cavity, infrared rays emanating from the operator 27 cause the infrared sensor 28 to operate and produce a signal for lighting the light source lamp. The lighting signal is transmitted through the signal lines 32 in the universal cord 8 to the light source unit 12. In the light source unit, it is amplified by the amplifier 34 and then is supplied to the Schmidt trigger circuit 36 where it is compared with the reference voltage Vref. The reference voltage Vref is preset to a level corresponding to a signal level of the signal which is produced and amplified when the operator 27 reaches a position within a predetermined distance from the eyepiece frame. Therefore, when the operator approaches the eyepiece frame to enter a range within the predetermined distance, the level of the signal applied to the Schmidt trigger circuit 36 becomes larger than the reference voltage Vref. Accordingly, the output from the Schmidt trigger circuit 36 is at high level and the relay drive circuit 38 is driven. As a result, the relay 44 is driven to close the relay contact 42. The electric power from the power source for the light source is supplied to the lamp 14 which in turn lights up. The light emitted from the lamp 14 is condensed at the end face of the light guide 4 by the condensing mirror 16 and is guided into the light guide 4 to be used for illuminating the objective portion. When the operator 27 looks into the inside of the eyepiece frame 24, an image of the objective portion is transmitted to the eyepiece lens 26 through the image guide 2 and he can observe the image transmitted.

When the operator 27 completes the observation of the objective portion and departs from the eyepiece frame by the predetermined distance or more, a sensing value of infrared rays from the infrared sensor 28 decreases, so that the input signal to the non-inverting terminal of the operational amplifier of the Schmidt circuit 36 becomes smaller than the reference voltage Vref. Accordingly, the output signal from the Schmidt circuit 36 changes its state from high to low level, with the result that the relay drive circuit 38 stops its operation. Subsequently, the relay 44 is deenergized and the relay contact 42 is opened, so that the lamp 14 is turned off.

As described above, the light source lamp 14 can be automatically turned on only when the operator 27 goes near the eyepiece section 22. Therefore, even if the amount of light from the lamp 14 is set to a relatively large value, a large amount of light is not guided onto the light guide 4 for a long time, thereby preventing the light guide 4 from being burned.

Further, there can be prevented a situation that electronic parts in the light source unit 12 are adversely influenced by the heat emanated from the light source lamp 14 when the light source lamp 14 is left turned on for a long time. In the embodiment as mentioned above, even when the operator 27 is not near the infrared detector 27, the infrared sensor 28 senses the rays emitted from the lamp in a room or the infrared rays contained in natural light. An erroneous operation of the apparatus due to these infrared rays may be prevented by setting the reference voltage Vref to a proper value. The infrared sensor 28 is not limited to a case where it is mounted to the eyepiece frame 24 as the above-mentioned embodiment. For example, the sensor 28 may be provided on the surface of the operating section 30 of the endoscope 6, whereby to sense the infrared rays emitted from the hand of the operator 27. Alternately, it may be provided within the operating section 30 of the endoscope 6, whereby to sense the infrared rays emitted from the eye of the operator 27 and transmitted through the eyepiece 26.

Figure 4:
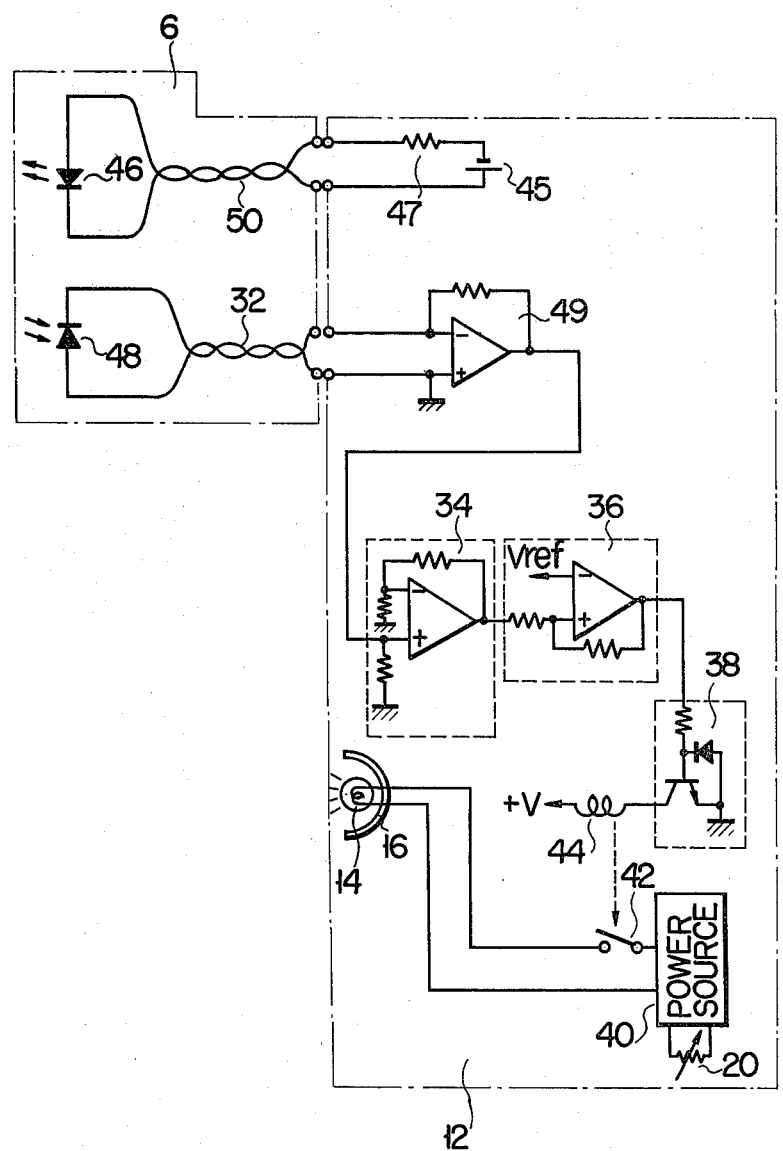
FIG. 4 is a circuit diagram of a light source controlling circuit of the light source unit to be assembled into the endoscope shown in FIG. 3.

In the embodiment shown in FIGS. 1 and 2, the approach of the operator is sensed by the infrared sensor 28. The sensor 28 may be replaced by the combination of a light emitting element such as a light emitting diode 46, and a light detecting element such as a photo diode or a photo transistor. Specifically, as shown in FIG. 4, a light emitting element 46 is provided to the eyepiece frame 24. Power supply lines 50 from the light emitting element extend to the light source unit 12, through the operating section 30 of the endoscope 6 and the universal cord 8. In the power source unit 12, the power supply lines 50 are coupled with a DC power source 45, through a resistor 47. The light detecting element 48 is fixed at a location on the eyepiece frame 24 which is adapted for receiving the light reflected from the face of the operator 27 near the eyepiece frame 24. The light detecting element 48 is connected to a current-voltage converter 49, through the signal lines 32 in the universal cord 8. The output of the current-voltage converter is connected to the Schmidt circuit 36 through an amplifier as in the embodiment shown in FIG. 2. The arrangement of the remaining portion of the light source unit is the same as that in the above-mentioned embodiment, and therefore it will not be described.

According to the present invention, when the operator 27 approaches the eyepiece frame 24, an illumination spot is produced on the operator's face by the light from the light emitting element and the light reflected from the illumination spot is projected into the light detecting element 48. When the operator 27 approaches the eyepiece frame within a predetermined distance, the signal level of the light detecting element 48 is increased to the preset value. Therefore it is possible to energize the light source. On the other hand, it is decreased as he goes away from the eyepiece frame 24. When he departs from it by a predetermined distance or more, only the light rays from the room lamp or the natural light is incident on the light receiving element 48. Therefore, it is impossible to energize the light source lamp 14.

Figure 5:
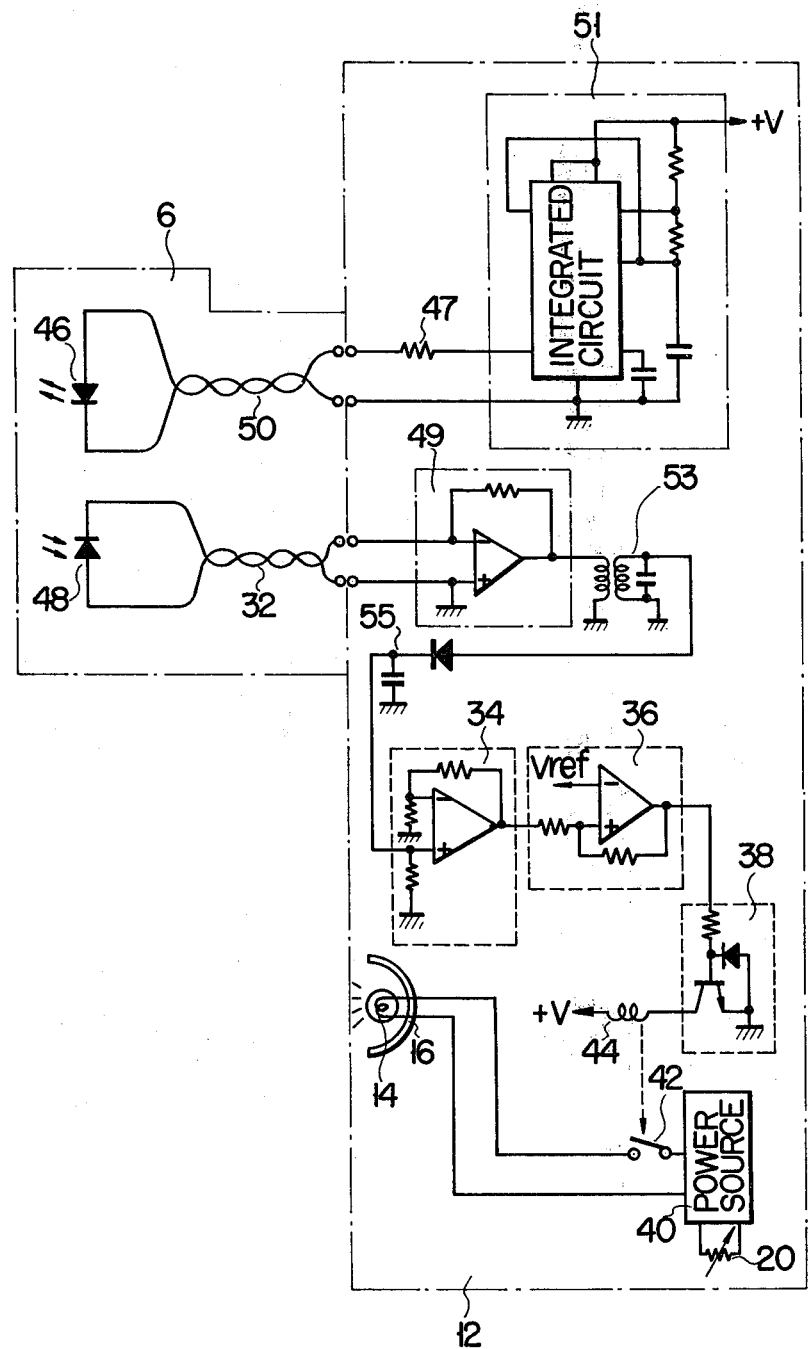
FIG. 5 is a circuit diagram of a modification of the light source controlling circuit shown in FIG. 4.

There is a possibility that the light source controlling circuit 18 erroneously operates due to the light from the room lamp or the natural light. This problem, however, can be solved in a manner that a current fed to the light emitting element 46 is previously AC-modulated, the output signal transmitted from the light detecting element 48 is electrically filtered, and the light source controlling circuit 18 is operated only by the optical signal from the light emitting element 46. As shown in FIG. 5, the light emitting element 46 is connected through the power supply lines 50 and the resistor 47 to an oscillating circuit 51 composed of an integrated circuit as NE555 manufactured by Texas Instruments Company, for example. Accordingly, the light emitting element 46 is lit at a frequency determined by the oscillating circuit 51. When the operator 27 approaches the eyepiece frame 24 within a predetermined distance from the frame 24, the light which is emitted from the light emitting element 46 and light-intensity modulated, is reflected by the face of the operator 27 and introduced into the light detecting element 48. Since not only the light-intensity modulated light but also the natural light or the room light as noise is incident on the light receiving element 48, the current signal at a fixed frequency containing the noise is produced from the light receiving element 48. A band-pass filter 53 and a rectifying circuit 55 are connected between a current-voltage converter 49 for converting the mixture current signal into a voltage and an amplifier 34. Therefore, only a voltage signal of a given frequency component is extracted, by the band-pass filter 53, from the mixture voltage signal derived from the converter 49. The voltage signal of the given frequency is applied to a rectifying circuit 55 where it is rectified. The rectified signal is applied to the Schmidt trigger circuit 36, by way of the amplifier 34. Accordingly, supplied to the Schmidt trigger circuit 36 is only a signal for measuring a distance which has a level dependent only on a distance between the eyepiece frame and the face of the operator 27. As a result, it correctly judges whether or not the distance is within a given range.

According to the present embodiment, an intensity of the light emitted from the light emitting element 46 may be weak because of the use of the electrical filter. By the weakness of the light, a situation can be prevented in which the operator is dazzled by the light from the light emitting element 46. Further, for obtaining a sufficient intensity of light from the light emitting element 46, it is preferable to use an infrared light emitting diode as the light emitting element 46.

It is not essential that the light emitting element 46 and the light receiving element are provided in the eyepiece section 22. For example, the light emitting and detecting elements 46, 48 may be provided in the light source unit 12 and optically coupled with one end of optical fibers (not shown), other ends of which are disposed at the eyepiece section 22, whereby to sense the approach of the operator.

Figure 6:
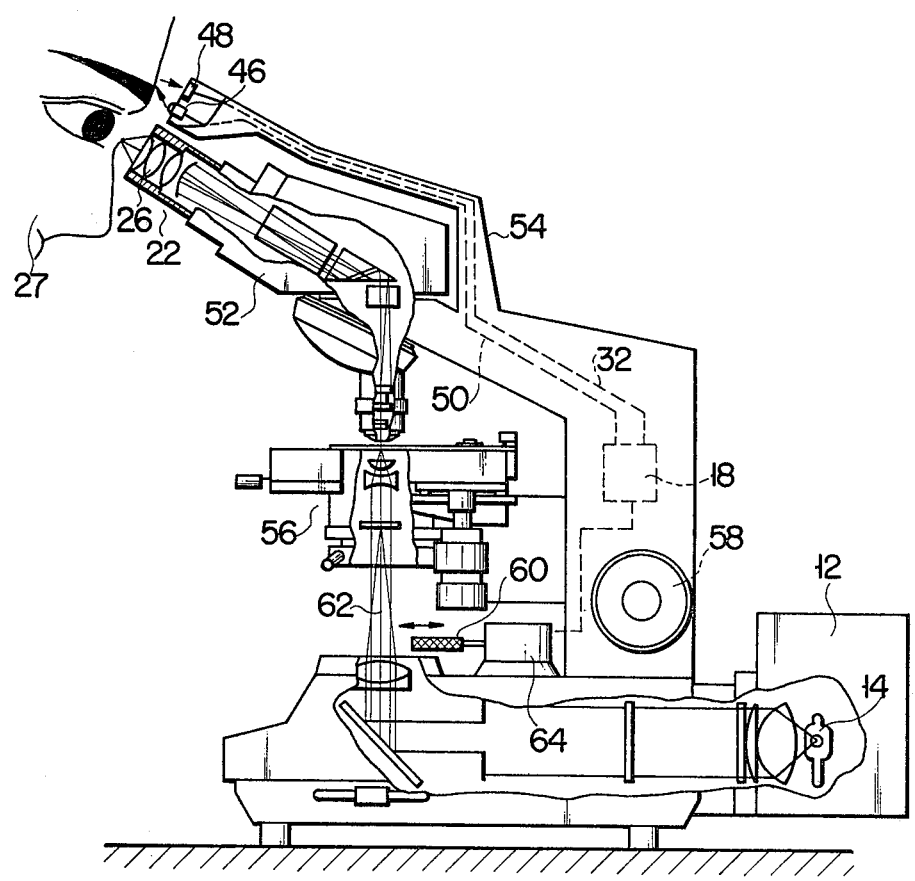
FIG. 6 is a schematic diagram of a microscope with a light source unit which is yet another embodiment of the present invention.

FIG. 6 shows another embodiment in which a light source unit according to the present invention is applied to a microscope of the transmitted illumination type. In the microscope, the eyepiece section 22 is removably coupled with a lens-barrel 52. Therefore, it is uneconomical to provide the element for sensing the approach of the operator 27 at the eyepiece section 22. Therefore, the microscope of the present embodiment is provided with an arm 54 extending from a microscope body having a handle 58 for focusing the microscope properly close to the eyepiece section 22. The light receiving element 48 and the light emitting element 46 are attached to the distal end of the arm 54, as in the embodiment shown in FIG. 3. The light receiving element 48 and the light emitting element 46 are connected to the light source lamp control circuit 18, by way of the signal line 32 and the power supply line 50, as previously stated. A shutter 60 is provided in the optical path of the light for illuminating a sample on the stage 56. The shutter 60 is mechanically coupled with the solenoid 64 so that it moves out of the optical path in response to a signal derived from the light source lamp control circuit 18.

According to the present embodiment, even if the light source lamp 14 is lit in the non-observing mode, the sample on the stage 56 is not illuminated since the shutter 60 is provided in the optical path. When the operator approaches the eyepiece section 22 for observing the sample, the light receiving element 48 senses the approach of the operator and the light source lamp control circuit 18 operates to drive the solenoid 64. As a result, the shutter 60 moves out of the light source path and the light illuminates the sample. Accordingly, the operator 27 can perform the ordinary observation of the sample. When the operator 27 finishes his observation and departs from the eyepiece section 22, the solenoid 64 is deenergized and the shutter 60 is again located in the optical path.

As described above, the light illuminates the sample only in the observing mode. Therefore, the sample is not changed in its nature. Further, it is not necessary to open the light source switch in the non-observing mode. The microscope is effectively operated to allow the operator to concentrate his attention only on the observation. In the above-mentioned embodiment, the shutter 60 is removably located in the light source path. Alternately, the power supply to the light source lamp 14 is shut off in the non-observing mode, as in the above-mentioned embodiment. With such an arrangement, the temperature rise of the light source unit is limited by the heat emanating from the light source lamp 14. Further, such an accident is prevented that the heat from the light source unit causes the microscope main body to thermally expand, resulting in deformation of the microscope main body and defocusing of the microscope.

Figure 7:
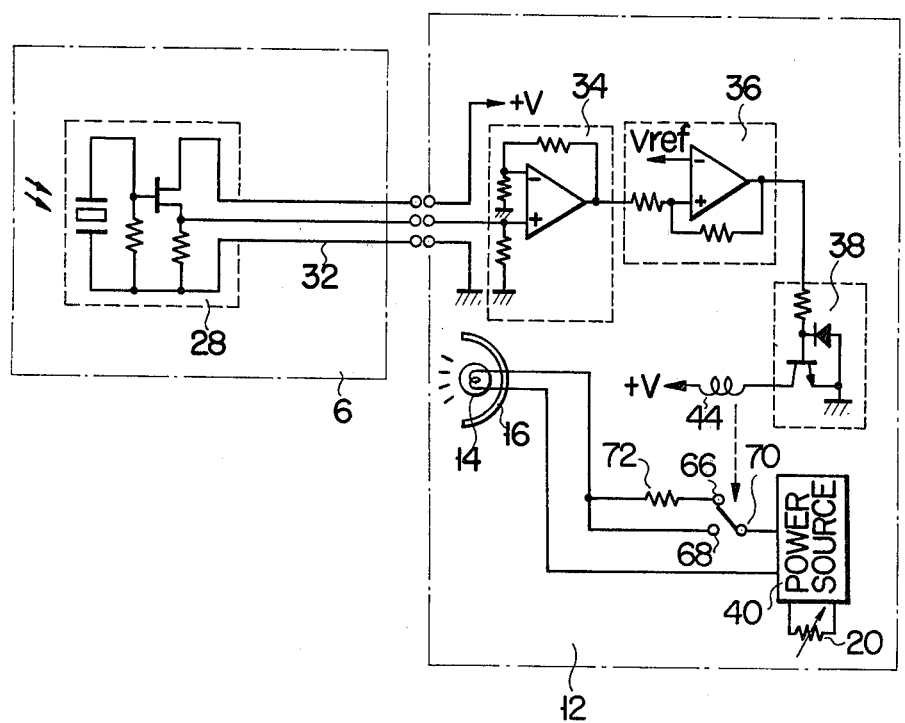
FIG. 7 is a circuit diagram of a modification of the light source controlling circuit shown in FIG. 2.

There have been described an example in which the illuminating light is shut off by means of a shutter provided in the optical path and another example in which the light source lamp is turned off. In yet another example, the intensity of light of the light source is reduced in the non-observing mode. For example, the relay 44 is provided with a movable contact 70 and first and second fixed contacts 66 and 68, as shown in FIG. 7. The second stationary contact 68 is directly connected to the light source 14, while the first stationary contact 66 is connected through the resistor 72 to the light source 14. When the relay 44 is not operated, that is, when the operator 27 is not near the eyepiece section 22, the movable contact 70 is coupled with the stationary contact. The current supplied from the power source 40 to the light source 14 is limited by the resistor 72, thus limiting the luminance brightness of the light source. When the observer 29 approaches the eyepiece section 22, the relay 44 is energized to turn the movable contact 70 to the second stationary contact 68. Accordingly, the power source 40 feeds current to the light source 14, not through the resistor 72, with the result that the light source 14 lights at a satisfactory luminance brightness. The embodiment shown in FIG. 7 is so designed that, when the operator is separated from the eyepiece section by a given distance or more in the non-observing mode, the power supplied to the light source lamp is decreased to adjust the light source luminance brightness. With this design, it is possible to prevent the burning of the end face of the light guide or the nature change of the sample. Further, even when trouble occurs which makes it impossible to sense the approach of the operator, the area to be observed can be observed satisfactorily. In addition to the circuit for sensing the approach of the operator, another circuit may be provided which is capable of always supplying the illuminating light and allows a manual operation of the light source lamp control circuit.

As described above, the light source unit according to the present invention energizes the light source at the maximum luminance brightness only in the observing mode and supplies the illuminating light to the objective portion at the maximum intensity. Therefore, it is possible to prevent the burning of the optical apparatus or the nature change of the sample. Additionally, in the observing mode, the area to be observed can clearly be observed with the illuminating light of a sufficient amount of the light.

We claim:

1. A light source unit for an optical apparatus having an eyepiece section comprising:
   a light source for transmitting illuminating light for illuminating an area to be observed;
   a power source for supplying electrical power to said light source;
   sensing means for sensing the presence of an operator at said optical apparatus for observing said area and for emitting an output signal indicating said presence or absence of an operator at said optical apparatus;
   a judging circuit coupled to said sensing means and responsive to said output signal from said sensing means indicating that the operator is absent from said optical apparatus, for producing a light emitting signal for limiting said illuminating light; and
   limiting means coupled to said judging circuit and being responsive to said light limiting signal for limiting the illuminating light transmitted from said light source to said area as a function of said light limiting signal.

2. A light source unit according to claim 1, wherein said illuminating light limiting means includes switch means for shutting off electrical power supplied from said power source to said light source responsive to said light limiting signal.

3. A light source unit according to claim 1, wherein said illuminating light limiting means includes a solenoid energized responsive to said light limiting signal; and a shutter which is located on an illuminating light path extending from said light source to the area to be observed, said shutter being coupled to said solenoid for shutting off the supply of said illuminating light to said area to be observed responsive to energization of said solenoid.

4. A light source unit according to claim 1, wherein said illuminating light limiting means includes a resistor coupled so as to restrict said electrical power supplied from said power source to said light source for thereby decreasing the luminance brightness of said light source; and switch means for coupling said resistor between said light source and said power source in response to said light limiting signal.

5. A light source unit according to claim 1, wherein said sensing means is an infrared sensor which senses infrared rays radiated from an operator.

6. A light source unit according to claim 1, wherein said sensing means includes a light emitting element which emits light toward an operator; and a light receiving element which senses light reflected from said operator and produces a sensing signal responsive to sensing of said reflected light.

7. A light source unit according to claim 6, wherein said sensing means includes an oscillating circuit which supplies current modified by a specific frequency to said light-emitting element and produces light-intensity modulated light, and a filter circuit which extracts only a specific frequency component from said esnsing signal produced from said light receiving element.

8. A light source unit according to claim 1, wherein said sensing means is provided at said eyepiece section of said optical apparatus for sensing the presence of an operator at said eyepiece section.

9. A light source unit according to claim 1, wherein said optical apparatus comprises an endoscope system having an image guide and a light guide; and said illuminating light is supplied from said light source to said light guide; and said illuminating light limiting means includes means for restricting the amount of light received by said light guide from said light source.

10. A light source unit according to claim 1, wherein said optical apparatus comprises a microscope having a stage for receiving a sample to be observed; and said illuminating light is supplied from said light source to said stage; and said illuminating light limiting means includes means for restricting the amount of light received by said stage from said light source.

11. A light source unit according to claim 1, wherein said sensing means includes means for sensing the presence of an operator who is within a pretermined distance from said optical apparatus.

12. A light source unit according to claim 8, wherein said sensing means comprises means for sensing the presence of an operator within a predetermined distance from said eyepiece section.

13. A light source unit according to claim 1, wherein said judging circuit includes means responsive to said output signal from said sensing means for producing said light limiting signal when the operator is judged to be more than a given distance from said optical apparatus.

14. A light source unit according to claim 8, wherein said judging circuit includes means responsive to said output signal from said sensing means for producing said light limiting signal when the operator is judged to be more than a given distance from said eyepiece section.

* * * * *

UNITED STATES PATENT AND TRADEMARK OFFICE
CERTIFICATE OF CORRECTION

PATENT NO. : 4,415,952
DATED : November 15, 1983
INVENTOR(S) : Shinichiro HATTORI et al It is certified that error appears in the above-identified patent and that said Letters Patent is hereby corrected as shown below:

IN THE ABSTRACT:

Line 11, the word "to" should be deleted;

Column 2, line 40, "being faced to" should read --facing--;

Column 8, line 8 (claim 7), "sensing means includes" should read --sensing means _further_ includes--;

line 11 (claim 7), "light," should read --light;--;

line 12 (claim 7), "esnsig" should read --sensing--.

Signed and Sealed this

Twenty-fourth Day of April 1984

[SEAL]

Attest:

GERALD J. MOSSINGHOFF

Attesting Officer   Commissioner of Patents and Trademarks